US005395754A

United States Patent [19]
Lambotte et al.

[11] Patent Number: 5,395,754
[45] Date of Patent: Mar. 7, 1995

[54] MEMBRANE-BASED IMMUNOASSAY METHOD

[75] Inventors: Paul P. Lambotte; Robert C. Darter, both of San Diego; Mark J. Sarno, Escondido, all of Calif.

[73] Assignee: Hybritech Incorporated, San Diego, Calif.

[21] Appl. No.: 923,339

[22] Filed: Jul. 31, 1992

[51] Int. Cl.⁶ .......................................... G01N 33/573
[52] U.S. Cl. ................... 435/607.4; 435/7.92; 435/7.94; 435/17; 435/967; 435/969; 435/970; 436/523; 436/527; 436/531; 436/533; 436/534; 436/535; 436/548
[58] Field of Search .............. 436/518, 523, 527, 529, 436/531, 532, 533–535, 548; 435/7.4, 7.92, 7.94, 17, 967, 969, 970; 422/69, 70; 427/2; 428/357, 361, 402.24, 403

[56] References Cited

U.S. PATENT DOCUMENTS

| | | | |
|---|---|---|---|
| 3,811,840 | 5/1974 | Bauer et al. | 436/518 |
| 4,059,407 | 11/1977 | Hochstraser | 422/56 |
| 4,264,766 | 4/1981 | Fischer | 536/51 |
| 4,313,734 | 2/1982 | Leuvering | 436/525 |
| 4,366,241 | 12/1982 | Tom et al. | 435/7.9 |
| 4,373,932 | 12/1983 | Gribnau et al. | 436/501 |
| 4,376,110 | 3/1983 | David et al. | 436/513 |
| 4,478,946 | 10/1984 | Van der Merwe et al. | 436/518 |
| 4,504,582 | 3/1985 | Swann | 435/108 |
| 4,506,015 | 3/1985 | Ho et al. | 435/175 |
| 4,624,916 | 11/1986 | Shah et al. | 435/17 X |
| 4,632,901 | 12/1986 | Valkirs et al. | 435/5 |
| 4,703,017 | 10/1987 | Campbell | 436/501 |
| 4,727,019 | 2/1988 | Valkirs et al. | 435/5 |
| 4,740,468 | 4/1988 | Weng et al. | 435/7.91 |
| 4,775,636 | 10/1988 | Moeremans | 436/518 |
| 4,837,168 | 6/1989 | de Jaeger | 436/533 |
| 4,843,000 | 6/1989 | Litman, I | 435/7.9 |

(List continued on next page.)

OTHER PUBLICATIONS

Bangs, L., "Latex Immunoassays," J. Clin. Immunoassay, 13 127–131 (1990).

(List continued on next page.)

*Primary Examiner*—Carol A. Spiegel
*Attorney, Agent, or Firm*—Donald J. Pochopien; Paul C. Steinhardt

[57] ABSTRACT

The present invention is directed to a membrane-based immunoassay method for an analyte of interest having at least two sterically separate antigenic sites. The method comprises providing a reactive membrane having a calibration zone and a test zone, wherein the calibration zone is characterized by having a predetermined amount of the analyte of interest immobilized via a first antibody as a first specific binding pair to a solid phase, the immobilized first binding pair being covalently cross-linked such that any remaining binding sites on said first immobilized antibody are substantially incapable of further specifically binding to any additional analyte, but at least some of said analyte is capable of specifically binding to a preselected amount of a labelled second antibody. The method further includes the steps of contacting the reactive membrane with a predetermined amount of sample and allowing any analyte in the test sample to become specifically bound to immobilized first antibody in the test zone; contacting the immobilized analyte in the test and calibrator zones with a labelled second antibody capable of binding to a second antigen site on the immobilized analyte; and determining the presence or amount of analyte in the test sample by comparing the amount of labelled second antibody specifically bound in the test zone versus the amount of labelled second antibody specifically bound in the calibration zone.

20 Claims, No Drawings

U.S. PATENT DOCUMENTS

| | | | |
|---|---|---|---|
| 4,849,338 | 6/1989 | Litman, II | 435/7.9 |
| 4,877,745 | 10/1989 | Hayes et al. | 436/166 |
| 4,895,809 | 1/1990 | Schlabach et al. | 436/518 |
| 4,916,056 | 4/1990 | Brown, III | 435/7.9 |
| 4,992,385 | 2/1991 | Godfrey | 436/525 |
| 5,030,558 | 7/1991 | Litman et al. | 435/7.91 |
| 5,120,662 | 6/1992 | Chan et al. | 436/530 |
| 5,169,754 | 12/1992 | Siiman et al. | 435/5 |

OTHER PUBLICATIONS

Bangs, L., "Particle-Based Tests And Assays–Pitfalls And Problems In Preparation," Am. Clin. Lab. News Editon, 9, 16–17 (1990).

Anderson et al., "Internally Referenced ImmunoConcentration TM Assays," Clin. Chem., 32 1692–1695 (1986).

Bangs, L., "Uniform Latex Particles," American Clinical Products Review, 7, 22–26 (1988).

Bangs, L., "New Developments In Particle-Based Tests and Immunoassays," J. Int. Fed. Clin. Chem., 2, 188–193, (1990).

Patent Abstracts of Japan, vol. 14, #531, Nov. 21, 1990 T. Higuchi, "Immuno Affinity Matrix".

Seradyn, Inc. "Microparticle Immunoassay Techniques" 2nd Edition 1988 pp. 4, 6, 9, 26–27.

Seradyn, Inc. "Uniform Latex Particle", 1984, pp. 3, 15, 38–39.

MEMBRANE-BASED IMMUNOASSAY METHOD

BACKGROUND OF THE INVENTION a. Field Of The Invention

The present invention is directed to a stabilized internal calibrator for use on a membrane-based test device, particularly a diagnostic test device as used in human and veterinary medicine. More particularly, the present invention is directed to a covalently cross-linked antigen-antibody complex for use as a stabilized internal calibrator on a calibration zone of any membrane-based device. In the present invention, the stabilized internal calibrator is more resistant to degradative processes, such as oxidation, enzymatic digestion and leaching, and requires less components and steps than conventional internal calibration systems.

b. Background

Membrane-based test devices, particularly those devices used in diagnostic and veterinary medicine, employ a variety of internal and external calibrators to provide a qualitative or a quantitative result for an analyte of interest in a test solution. One type of membrane-based test device is the dipstick. The dipstick is a stick having a small reagent impregnated membrane at one end for dipping into a test solution either containing or suspected of containing the analyte of interest. The dipstick membrane (hereinafter "dipstick") develops a color that is proportional to the concentration of the analyte of interest in the test sample. Typically, the user determines the concentration of the analyte by comparing the color on the membrane to the color on an external calibrator, such as a series of colored plates that are printed on a label. The color of each plate is associated with a particular concentration of the analyte. The color on the plate that most closely approximates the color on the dipstick provides the user with an approximate concentration of the analyte in the test sample.

External calibration of a dipstick, via colored plates, has several problems. First, it is difficult to match the color of the plates with the color on the dipstick. Secondly, the color on the plates would not fade in proportion to the adverse conditions affecting the color on the dipstick. Further, the color on the plates would at best only be accurate for a particular set of reaction conditions. However, in the normal clinical situation, the dipstick reaction is often performed at other than the calibration conditions.

Accordingly, it is an object of the present invention to provide a stabilized internal calibrator for a dipstick that would compensate for conditions affecting the test reagents prior to and during their reaction with the analyte of interest.

More recently, the color produced by a dipstick that has been dipped into a test sample is read on an instrument. Prior to reading the color produced by a test sample, the instrument is calibrated against the color produced by a second dipstick that has been exposed to a known concentration of analyte. The dipstick method suffers from several problems. The first problem with this dipstick method is that it requires two dipsticks. Secondly, the instrument may have drifted from the values set in its last calibration, which may have only been hours before. Further, the reaction conditions between the calibrator and the test sample may have been different, either with respect to time or reaction temperature. Accordingly, it is an object of the present invention to eliminate the need for two dipsticks to calibrate a dipstick reaction. It is a further object of the present invention to insure that the calibrator and test sample are exposed to the same reaction conditions.

A second type of membrane-based test device is the ICON® type device of Hybritech's U.S. Pat. Nos. 4,632,901, 4,727,019 and 5,120,504. Although the word Immunoconcentration™ (also known as ICON®) is a trademark of Hybritech Incorporated, other manufacturers of a similarly functioning devices, such as Pacific Biotech, Inc., refer to their device as an immunosorbent assay. In either of these devices, an excess amount of the binding partner to the analyte of interest is immobilized, typically as a test spot, on a membrane that is positioned over an absorbent pad. The pad is in liquid receiving relationship with the membrane. When an aliquot of a test sample that is suspected of containing the analyte of interest is placed on the membrane, it is wicked through the membrane and into the absorbent pad. Any analyte of interest that passes through the test spot on the membrane is bound to its binding partner immobilized thereon. A reagent containing a labeled second binding partner to the analyte is poured onto the membrane. As it passes through the membrane, the labeled binding partner to the analyte of interest binds to any immobilized analyte at the test spot thereon in proportion to the amount of analyte that has been immobilized. Ultimately, a color is produced at the test spot on the membrane in proportion to the amount of analyte immobilized thereon.

In the ICON® type devices, it is desirable to provide the user with an internal reference, such as a calibration or reference spot, that produces a visible colored signal in proportion to a known concentration of an analyte of interest. This internal reference allows the user of the ICON® type device to obtain a semi-quantitative result (i.e., a result reported as greater than, equal to, or less than the calibrator). To obtain the semi-quantitative result, the user of the ICON® type device visually compares the color produced at the test spot relative to the color produced at the calibration spot and determines whether it is greater than, equal to, or less than the color produced by the known concentration of the calibrator at the calibration spot. Alternatively, the user of the device can quantitate the concentration of the analyte of interest by instrumentally measuring the color of the known reference and the color of the unknown sample, such as by reflectance, and solving an equation for the concentration of analyte in the unknown.

One method for providing an internal reference in an ICON® type device involves binding (i.e., immobilizing) a second antibody, typically in the shape of a spot, to a discrete portion of the membrane. Alternatively, the second antibody may be immobilized on a plurality of microparticles that themselves have been immobilized, such as by trapping or bonding, to a discrete spot on the membrane's surface. See Anderson et al., "Internally Referenced Immuno-Concentration™ Assays," *Clin. Chem.*, 32 1692–1695 (1986). Unlike the first antibody at the test spot, the second antibody at the reference spot is not specific for the analyte of interest. Rather, it is specific for an exogenous substance that is selectively foreign to the test samples suspected of containing the analyte of interest. The second antibody is bound to a sufficient amount of the exogenous substance such that when the exogenous substance is labeled, the reference spot produces a detectable signal at a level that corresponds with the signal produced by a known amount of the analyte of interest that has become immobilized and labeled at the test spot under those reaction conditions.

The above method of providing an internal reference using an exogenous substance is laborious due to the necessary cross referencing between the parallel series of reactions involving the analyte and the exogenous substance.

It is also an object of the present invention to eliminate the manufacturing difficulties (i.e., laboriousness) associated with having a different reaction series for the reference and the analyte of interest.

Attempts to utilize the same immobilized antibody on both the test spot and the reference spot have most often failed. Antibodies have two binding sites. When a known amount of the analyte of interest is bound to the antibody on the reference spot, there is no assurance that all of the antibody binding sites on the reference antibody have been occupied. Further, the desirable signal level for the reference spot may require a less than saturating amount of antibody. Accordingly, when a test solution containing analyte of interest is added to the test device, the analyte of interest is capable of binding both to the antibody on the test spot and to the available sites on the identical antibody on the reference spot. As a result, the amount of analyte that is bound to the antibody at the reference spot is influenced by the amount of analyte that is in the test sample. Thus, any signal produced at the reference spot would be upwardly biased as a function of the amount of analyte in the test sample. Consequently, highly elevated concentrations of analyte in a test sample would be reported artificially low relative to their actual values. Accordingly, it is an object of the present invention to produce an internal calibrator for an immunosorbent device that would be stable under differing reaction conditions but that would not be influenced by the amount of analyte in a test solution.

A third type of membrane-based test device that also has applications in diagnostic and veterinary medicine is the immunochromatography test device. Immunochromatography test devices of various types have been known to the art for years. In test devices of the immunochromatography type, a sample that is suspected of containing the analyte of interest is placed at or near one end of a membrane strip. The sample is allowed to be carried to the opposite end of the membrane strip by a liquid phase that traverses the membrane strip by capillary action. While traversing the membrane strip, the analyte in the test sample, if any, encounters one or more reagents with which it may react to produce a detectable signal. The early types of immunochromatography devices, such as taught in U.S. Pat. No. 4,366,241 (Tom et al.), lacked an internal reference. Later devices, such as taught in U.S. Pat. No. 4,374,925 (Litman) employed an internal reference. In some instances, the internal reference was analogous to that described for the ICON ® devices and suffered from the same laborious cross-referencing. In other instances, the internal reference served the function of merely validating a positive signal at the reaction zone, such as by capturing a labeled antibody at a point beyond the reaction zone.

Thus, it is a further object of the present invention to provide an internal calibrator for use with an immunochromatography device that solves the problems in common with the immunosorbent type devices and/or that renders the immunochromatography device capable of approximating the amount of an analyte of interest in a test sample. It is also an object of the present invention to provide an internal calibration zone on a membrane-based device that reflects the stability of the reagents thereon and that is capable of providing a stable calibration signal for calculating the concentration of an analyte of interest in the test sample.

SUMMARY OF THE INVENTION

The present invention is directed to a stabilized internal calibrator for use on any membrane-based test device that is capable of detecting the presence and/or amount of an analyte of interest in a test solution. The calibrator comprises a microparticle having bound thereto a predetermined amount of a first binding partner to the analyte of interest, the first binding partner further being non-covalently bound to a second predetermined amount of the analyte of interest and forming an immobilized binding pair therewith, the first binding partner and the analyte of interest of the immobilized binding pair also being covalently cross-linked to one another by an effective amount of a cross-linking agent, such that the amount of the analyte of interest immobilized on the microparticle becomes substantially fixed, the effective amount of the analyte of interest having an area on its surface or a cavity sufficiently exposed to be capable of participating in the formation of a second binding pair with a labeled second binding partner thereto.

The stabilized internal calibrator of the present invention is preferably used to produce an internal calibration zone for use on any membrane-based test device. The calibration zone is or includes a portion of the membrane-based test device having bound or deposited thereon an amount of the stabilized internal calibrator of the present invention that is effective for calibrating the results obtained on the device.

The present invention is further directed to a method for making a stabilized internal calibrator for a membrane-based test device comprising the steps of:

a. allowing a first binding partner of the analyte of interest and the analyte of interest to form a binding pair;

b. either before or after Step (a), bonding the first binding partner to a microparticle, whereupon after the combination of Steps (a) and (b), an immobilized binding pair is formed; and c. reacting the immobilized binding pair with an effective amount of a cross-linking agent for covalently cross-linking the analyte of interest and the first binding partner of the immobilized binding pair to one another such that an effective amount of the analyte of interest immobilized thereon becomes substantially fixed thereon, the effective amount of the analyte of interest also having a portion sufficiently exposed to be capable of participating in the formation of a second binding pair with a labeled second binding partner.

The method of the present invention not only produces the calibrator of the present invention, but it may be utilized en route to producing a calibration zone for any membrane based test device by further including the additional step of depositing on a portion of the membrane of a membrane-based test device an effective amount of the stabilized internal calibrator of the present invention to provide a calibration zone that is capable of internally calibrating the membrane-based test device.

DETAILED DESCRIPTION OF THE INVENTION

The present invention has multiple aspects. In its first aspect, it is directed to a stabilized (i.e., cross-linked) internal calibrator for use with a membrane-based test device, any membrane-based test device, which device is capable of detecting the presence and/or concentration of an analyte of interest in a test solution. The stabilized internal calibrator of the present invention comprises a microparticle having bound thereto a predetermined amount of a first binding partner to an analyte of interest, the first binding partner further being non-covalently bound to a second predetermined amount of the analyte of interest and forming an immobilized binding pair therewith, the first binding partner and the analyte of interest of the immobilized binding pair also being covalently cross-linked to one another by an effective amount of a cross-linking agent such that the effective amount of the analyte of interest immobilized on the microparticle becomes substantially fixed, the effective amount of the analyte of interest having an area on its surface or cavity sufficiently exposed to be capable of participating in the formation of a second binding pair with a labeled second binding partner.

The stabilized internal calibrator of the present invention exhibits its increased stability both in liquid suspension and in dry form such as when deposited on the membrane of a membrane-based device.

The first two components of the stabilized internal calibrator of the present invention are the analyte of interest and its binding partner. For purposes of describing the present invention, an "analyte of interest" and its "binding partner" are the two members of an immunologic pair. A "member of an immunologic pair" is one of two different molecules wherein one of the molecules has an area on its surface or a cavity which specifically binds to a particular spacial and polar organization of the other molecule. The members of the immunologic or binding pair are referred to herein as a "ligand" and "antiligand." A "ligand" is an organic or biochemical compound for which an antiligand naturally exists or can be prepared, e.g., hCG. An "antiligand" is any macromolecular compound, composition, or fragment thereof that is capable of recognizing (as manifested by an enhanced binding affinity to) a particular spatial and polar organization of a molecule, i.e., an epitopic or a determinant site. By way of example, antiligands include naturally occurring compounds, such as intrinsic factor, thyroxine-binding globulin, antibodies, enzymes, lectins, biotin, avidin, strepavidin, c-DNA and the like, and compounds prepared by human intervention, such as monoclonal antibodies, Fab or Fab' fragments, DNA probes, antisense strands of DNA, and the like.

The analyte component of the stabilized internal calibrator preferably has at least two sites (e.g., epitopes) that are each capable of forming a binding pair with their respective binding partner. However, it is sufficient for the analyte of interest to have a single binding site for a binding partner, if the analyte in combination with the first binding partner is capable of producing a unique binding site for a second binding partner, preferably a binding partner, e.g., an antibody, bearing a label.

Analogs of an analyte of interest may also be used when the analyte of interest is a biochemical entity. An "analog of the analyte of interest" is a compound that for purposes of the particular assay behaves substantially the same as the analyte of interest. For example, when the analyte is an antigenic material that has multiple epitopes, it may only be necessary to use a fragment of the analyte that contains the epitope(s) of interest. In the case of vitamin $B_{12}$, it is also well known in the art that analogs of vitamin $B_{12}$ will also bind to intrinsic factor, an antiligand for vitamin $B_{12}$. Similarly, analogs of folic acid are also known in the art to bind to beta-lactoglobulin, an antiligand for folic acid. The substitution of an analog for the analyte of interest is well known to those of ordinary skill in the art.

U.S. Pat. No. 4,366,241 (Tom et al.), which is incorporated herein by reference, lists at columns 19–26 a variety of potential analytes of interest that are members of an immunologic pair, including proteins, blood clotting factors, hormones, microorganisms, pharmaceutical agents, and vitamins. Any of these analytes are suitable for use as the analyte component in the stabilized internal calibrator of the present invention. However, preferred analytes of interest are ligands that are antigenic. Examples of preferred ligands include the following: human bone alkaline phosphatase antigen (HBAPAg); human chorionic gonadotropin (hCG); human luteinizing hormone (hLH); human follicle stimulating hormone (hFSH); creatine phosphokinase MB isoenzyme; ferritin; carcinoembryonic antigen (CEA); prostate specific antigen (PSA); CA-549 (a breast cancer antigen); hepatitis B surface antigen (HBsAg); hepatitis B surface antibody (HBsAb); hepatitis B core antigen (HBcAg); hepatitis B core antibody (HBcAb); hepatitis A virus antibody; an antigen of human immunodeficiency virus HIV I, such as gp 120, p66, p41, p31, p24 or p17; the p41 antigen of HIV II; and the respective antiligand (preferably a monoclonal antibody) to any one of the above ligands. The HIV antigens are described more fully in U.S. Pat. No. 5,120,662 and in Gelderblood et al., Virology 156: 171–176 1987, both of which are incorporated herein by reference.

The third component of the stabilized internal calibrator of the present invention is a microparticle. As used herein, the word "microparticle" includes any particle or bead to which a binding partner of the analyte of interest may be bound, whether covalently, or non-covalently such as by adsorption. An additional requirement for any particle that is used in a quantitative assay is that the particle also not contribute a signal, usually light absorption, that would cause the zone in which the particles were located to have a different signal than the rest of the membrane.

In any application, the microparticles must be capable of being retained by the membrane whether by trapping or adhesion. For example, when a microparticle is subject to immersion, such as in a dipstick type device, or when subject to liquid flow, such as in an immunochromatography, ICON ® or immunosorbent type device, the microparticle must be capable of remaining substantially immobilized.

The microparticles may be of any shape but are preferably spherical. The nature of the microparticle may vary widely, being naturally occurring or synthetic, being a single material, a few materials, or a combination of a wide variety of materials. Naturally-occurring microparticles include nuclei, mycoplasma, plasmids, plastids, mammalian cells (e.g., erythrocyte ghosts), unicellular microorganisms (e.g., bacteria) and the like. Synthetic microparticles may be prepared from synthetic or naturally occurring materials, or combinations thereof. For example, latex microparticles may be prepared from a synthetic material such as styrene. Other microparticles may be prepared from naturally-occurring materials, such as polysaccharides, e.g., agarose, or the like. (See, e.g., Gould, et al., U.S. Pat. No. 4,837,168, which describes the use of a variety of particles.) Preferred microparticles are microspheres of latex (i.e., a natural or a synthetic polymer) or glass; more preferably microspheres of latex. The microspheres of glass or latex are also referred to in the art as "beads" or "microbeads."

The mean diameter for the microparticle component of the present invention is within the range from 0.01 $\mu$m to 100 $\mu$m, more typically from about 0.1 $\mu$m to about 75 $\mu$m. The mean diameter and type of the microparticle chosen for a particular application will depend upon the pore size of the membrane and/or its composition.

Latex microparticles for use in the present invention are commercially available as polymeric microspheres of substantially uniform diameter (hereinafter "polymeric microspheres"), such as from Bangs Laboratories, Carmel, Indiana, or Dow Chemical Co., Midland, Mich. Although any polymeric microsphere that is capable of adsorbing or of being covalently bound to a binding partner may be used in the present invention, the polymeric microspheres typically are composed of one or more members of the group consisting of polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchlorideacrylates and the like or an aldehyde, carboxyl, amino, hydroxyl, or hydrazide derivative thereof.

The underivatized polymeric microspheres, such as polystyrene, are hydrophobic and passively adsorb other hydrophobic molecules, including most proteins and antibodies. Techniques for adsorbing a protein or polypeptide on a hydrophobic particle are well known in the art. For example, see Cantarero, et al. "The Absorption Characteristics of Proteins for Polystyrene and Their Significance in Solid Phase Immunoassays," *Analytical Biochemistry* 105, 375–382 (1980); and Bangs, "Latex Immunoassays," *J. Clin. Immunoassay*, 13 127–131 (1980) both of which are incorporated herein by reference. Various procedures for adsorbing molecules on polymeric microspheres are also described, in general terms, in Bangs, L. B., "Uniform Latex Particles," presented at a workshop at the 41st National Meeting, Amer. Assoc. Clin. Chem., 1989, and available in printed form from Seragen Diagnostics Inc., Indianapolis, Ind.; or Galloway, R. J., "Development of Microparticle Tests and Immunoassays," Seradyn Inc. Indiana which is incorporated herein by reference.

Generally, to adsorb (i.e., to non-covalently bond) a binding partner of the analyte of interest onto a microparticle, one:

1) utilizes pure reagents;
2) optionally, cleans the microparticles prior to the coating; and
3) determines the quantitative surface coverage of the microparticle and the binding partner's chemistry.

Thereafter, the binding partner to the analyte of interest is dissolved in a buffer solution and to it is added a latex suspension. The resulting suspension is stirred for a time ranging from a few minutes to more than 24 hours. After equilibration, the suspension is centrifuged and the supernatant containing any unadsorbed binding partner is discarded. The resulting latex with the binding partner adsorbed thereon (i.e., the immobilized binding partner) is resuspended in fresh buffer and centrifuged. The supernatant is again discarded. These wash steps are repeated until the immobilized binding partner is determined to be free of any residual unadsorbed binding partner. At this juncture, the binding partner that has been immobilized on a microparticle by adsorption is ready for binding to its respective analyte of interest.

The covalent bonding of a binding partner to a microparticle may be accomplished either directly, such as by reacting an activated chemical functional group on the surface of a microparticle with an appropriate chemical functional group on the binding partner, or indirectly, such as by covalently binding the binding partner to a spacer molecule that has been covalently bound to the surface of the microparticle. For example, a carboxylate modified latex microparticle, such as a carboxylated polystyrene, is capable of being covalently bound directly to a ligand or to an antiligand that has free amino groups if the carboxyl groups are activated with a water-soluble carbodiimide, such as 1-ethyl-3-(3-dimethylaminopropyl)carbodiimide hydrochloride, which is commercially available from Pierce Chemical Co., Rockford, Ill. as Cat. No. 22980. Alternatively, a spacer may be coupled to the activated carboxyl group to allow the ligand or antiligand to be held away from the particles surface. Such a spacer may be a C-6 to C-20 hydrocarbon with an amino group at each of its two ends. When one end of such a spacer is covalently bound to a latex microparticle, such as the above described microparticle having an actual carboxyl group, the amino group at the second end of the spacer is available for covalent coupling to the binding partner of the analyte of interest. The covalent bonding of ligands or antiligands to carboxyl modified particles is more fully taught in U.S. Pat. Nos. 3,857,931, 4,181,636 and 4,264,766 which are incorporated herein by reference. See also Bangs, L. B., "Uniform Latex Particles" which has been incorporated herein by reference.

When a small binding partner, such as an Fab or an Fab' fragment, is to be bound to the microparticle, it is preferably done via a spacer molecule as described above or via either a protein (e.g., bovine serum albumin) or a polymer (e.g., dextran) that has been covalently bound or adsorbed on the microparticle's surface. Thus, in the present invention, a ligand or antiligand that is also a binding partner to the analyte of interest may be affixed to a polymeric microparticle by either non-covalent or covalent bonding. A preferred method of non-covalent bonding is adsorption.

The binding partner of the analyte of interest that is adsorbed on a polymeric microsphere is preferably an antibody or a binding fragment thereof that has specificity either for the analyte of interest, a fragment of the analyte of interest, or an analog thereof. More preferably, the binding partner is a monoclonal antibody or a binding fragment thereof and the polymeric microsphere is a polystyrene microsphere.

Antibodies suitable for use in this invention are obtained by techniques known to the art. For instance, polyclonal antibodies are obtained by immunizing a species of animal that differs from the species producing the antigen (analyte of interest). Monoclonal antibodies are obtained by fusing the splenocytes of an immunized mouse with a plasmacytoma cell line, such as HMS 3.3, by the addition of polyethylene glycol to the cell mixture, thereby forming hybridoma cells which are suspended and then plated to tissue culture plates. Only the cultures producing antibodies that are immunologically reactive with antigen are cloned. See for example U.S. Pat. No. 4,376,110 which teaches the preparation of monoclonal antibodies and is incorporated herein by reference.

While the foregoing discussion is in the context of latex particles, other microparticles as disclosed herein, such as glass, liposomal sacs, erythrocyte ghosts and the like may also be used.

The final component of the stabilized internal calibrator of the present invention is a cross-linking agent that is capable of covalently cross-linking the analyte of interest and the binding partner of the immobilized binding pair to one another. By covalently cross-linking the analyte of interest and the binding partner to one another, the cross-linking agent prevents their dissociation. If the binding partners are immobilized on the microparticle in sufficient proximity to one another, the cross-linking agent is also capable of covalently cross-linking the adjacently immobilized binding pairs to one another. The result is a stabilized internal calibrator comprising a plurality of binding pairs cross-linked to one another over a microparticle core somewhat analogous to a stitched baseball cover over its core. In both cases, the cross-linking (or stitching) of the surface components provides a cover that is not readily removable from the core.

A second function of the cross-linking agent is to block the unoccupied binding sites on the immobilized binding partner (e.g., antibody) of the immobilized binding pair. The blocking of the unoccupied binding sites further stabilizes the internal calibrator relative to the predetermined amount of the analyte of interest thereon by rendering the immobilized binding partner incapable of further binding to any analyte of interest that may be present in the test solution. As a result, the effective amount of the analyte of interest on the microparticle becomes fixed such that the internal calibrator of the present invention is not susceptible to being substantially biased by further binding to the analyte of interest in a test sample.

A third function unexpectedly performed by the cross-linking component of the present invention is the ability to stabilize a labile analyte component of the calibrator of the present invention. For example, the analyte creatine kinase-MB ("CK-MB") is both heat and light labile. The labileness of CK-MB arises in part because CK-MB has two subunits (i.e., an "M" subunit and a "B" subunit) that are held together by non-covalent bonds. The cross-linking component of the present invention apparently stabilizes the immobilized CK-MB in part by forming a covalent cross-link between the M subunit and B subunit to prevent their dissociation. The cross-linking agent is also capable of forming covalent cross links within the folds of the enzyme. These covalent cross-links then fix the conformation of the enzyme. By fixing the conformation of an analyte, such as CK-MB, the conformation of the binding site for the second binding partner is presumably also fixed. The fixed conformation of the binding site for the second binding partner also enhances the stability of the immobilized and cross-linked calibrator relative to an immobilized calibrator that has not been cross-linked.

The cross-linking agent that is used in the present invention may be a hetero- or a homobifunctional linker. The choice of a cross-linking agent for any particular case will depend upon the nature of the chemical functional group(s) that are available on the analyte of interest and on its binding partner for cross-linking. Preferably, the chemical functional group on the analyte that is chosen for linking should be located at a site on the analyte of interest other than the binding site for the labeled second binding partner.

Often, the analyte of interest and/or its binding partner are a protein or a polypeptide. The most common chemical functional groups on a protein that are suitable sites for cross-linking are the sulfhydryl group (—SH) of cysteine; the $\epsilon$-amino group (—$NH_2$) of lysine; the carboxyl (—COOH) group of aspartic acid, glutamic acid or of C-terminal amino acids; the thioether (—S—$CH_3$) of methionine; the imidazolyl group of histidine; the guanidinyl group of arginine; the phenolic group of tyrosine; and the indolyl group of tryptophan. A listing of proteins, which would have one or more of those functional groups, is taught in U.S. Pat. No. 4,366,241 (Tom et al.) at cols. 19–20, all of which is incorporated herein by reference. The conjugation of chemical agents to proteins, via these functional groups, is taught, for example, in "Chemistry of Protein Conjugation and Cross-Linking, " Wong Shen CRC Press, Boston, 1991, which is incorporated herein by reference.

Of the various chemical functional groups on an analyte of interest or its binding partner, the amino groups and the sulfhydryl group are preferred for use in cross-linking. Many proteins do not have free sulfhydryl groups. However, most proteins or polypeptides do have free amino groups, via the epsilon amino group of lysine, and the amino group at the N-terminus. Thus, as a practical matter, the amino group is more preferred.

Numerous hetero- and homobifunctional cross-linking agents are familiar to those of ordinary skill in the art. For example, for linking amino groups, one may use one or more homobifunctional cross-linking agents, such as the bisimidoesters (bisimidates), which include dimethyl suberimidate ("DMS"), dimethyl adipimidate ("DMA"), dimethyl pimelimidate ("DMP"), and the like, all of which are available as their dihydrochloride salts. Alternatively, one may use one of the bis-N-succinimidyl esters, such as disuccinimidyl suberate ("DSS") or the like; or one of the homobifunctional acrylating agents, such as 1,6-hexamethylene diisocyanate or the like.

For linking sulfhydryl groups, one may use one of the bismaleimides, such as N,N'-trimethylene bismaleimide, bis(N-maleimide methyl) ether and the like. Other multifunctional and bifunctional linking agents are taught in U.S. Pat. No. 5,118,791 which is incorporated herein by reference. A detailed listing of cross-linking agents and their use is taught in the book "Chemistry of Protein Conjugation and Cross-Linking" CRC Press (1991) Wong, S. S., which is incorporated herein by reference.

For cross-linking an amino group to a sulfhydryl group, one would use a heterobifunctional cross-linking agent. Examples of such heterobifunctional cross-linking agents include N-succinimidyl maleimidoacetate which is disclosed in Kitagawa et al., "Preparation and Characterization of Hetero-Bifunctional Cross-Linking Reagents For Protein Modifications," *Chem. Pharm. Bull.*, 29 1130 (1981) and incorporated herein by reference; N-succinimidyl-3-maleimidopropionate (BMPS), which is similarly disclosed in Kitagawa; N-succinimidyl bromoacetate which is commercially available such as from Calbiochem Biochemicals, San Diego, Calif.; and the like. Additional heterobifunctional cross-linking agents for cross-linking these and other functional groups are disclosed in Wong S. S., "Chemistry of Protein Conjugation and Cross-Linking" which has already been incorporated herein by reference.

A preferred cross-linking agent for cross-linking the analyte CK-MB to its preferred first binding partner, monoclonal anti CK-B, is disuccinimidyl suberate.

Regardless of the cross-linking agent, the stabilized internal calibrator of the present invention utilizes an amount of the cross-linking agent that is effective for covalently cross-linking the analyte of interest and the binding partner of the immobilized binding pair to one another, the analyte of interest of the immobilized and cross-linked binding pair having a portion sufficiently extending therefrom to be capable of participating in the formation of a second binding pair with a labeled second binding partner thereto. If too little cross-linking agent is used, the analyte of interest would not be cross-linked to its immobilized binding partner, and thus would be capable of dissociation therefrom. Also, the unoccupied binding sites on the immobilized binding partner would not be tied up (i.e., hindered) by the cross-linking agent and thus, would be capable of binding with any analyte of interest in the test sample. Conversely, if too much cross-linking agent is employed, the portion of the analyte of interest that participates in forming in a second binding pair with a labeled second binding partner would be blocked or modified, thereby precluding its participation in binding the second binding partner. Employing an even greater amount of cross-linking agent could cause the particles to bind to one another as evidenced by their clumping.

In determining an effective amount of a cross-linking agent, one of ordinary skill in the art would react the immobilized binding pair with increasing molar ratios of cross-linking agent to protein beginning with 1:1 at first and increasing, such as 10:1, 20:1, 50:1, 100:1, etc., until the analyte of interest and the binding partner of the immobilized pair were sufficiently cross-linked to resist dissociation from one another and the microparticle but not so cross-linked as to render the analyte of the stabilized internal calibrator incapable of forming a second binding pair with a second binding partner.

In a particularly preferred embodiment of the stabilized internal calibration of the present invention, the first binding partner to the analyte of interest is bound to the microparticle in a predetermined amount that is sufficient to place the individual immobilized binding partners in a cross-linkable proximity to one another. Thus, upon exposure of the immobilized binding pair to an effective amount of a cross-linking agent, the binding partners themselves become cross-linked to one another by the cross-linking agent, thereby forming a webbing that entraps the immobilized binding pair upon the particle's surface. An immobilized binding pair that was entrapped by such a webbing was very stable, i.e., it was capable of withstanding exposure to boiling aqueous sodium dodecyl sulfate without a detectable loss of the bound protein.

On occasion, it may be necessary or preferable to prevent a chemical functional group that is located at a binding site on the immobilized analyte from participating in the cross-linking reaction. The selection of a protecting group for a particular binding site is dependent upon the chemical functional groups that make up the binding site. These chemical functional groups typically include sulfhydryl, amino, carboxyl and hydroxyl. Suitable protecting groups for each of these functional groups are known in the art and taught in the Gross et al., "The Peptides: Analysis, Structure and Biology, " Vol 3 "Protection of Functional Groups in Peptide Synthesis" (Academic Press, New York, 1981). Any protecting group that is chosen must render the protected group inert under the conditions employed in the cross-linking reaction and must be readily removable after the cross-linking reaction without altering the binding site or adversely affecting the integrity of the immobilized and cross-linked (i.e., stabilized) binding pair. By way of example, some of the useful protecting groups for the alpha amino groups of a protein or a polypeptide or for the epsilon-amino group of a lysine residue are the following: t-butoxycarbonyl ("BOC"), p-chlorobenzyloxycarbonyl, t-amyloxycarbonyl and the like.

The stabilized internal calibrators of the present invention are particularly useful as internal calibrators for a membrane-based test device. By the word "membrane" as used in the phrase "membrane-based test device," is meant any porous capillarity possessing or bibulous material through which an aqueous solution containing an analyte of interest may pass. Materials that provide a suitable matrix for use as the membrane component of a membrane-based test device include the following: the various cellulose-fiber containing materials, such as filter papers, chromatographic paper, ion exchange paper, cellulose acetate films, nitrocellulose films, cellulose acetate discs, cellulose thin layer chromatography discs and the like; the starch based materials, such as SEPHADEX ® brand cross-linked dextran chains, polyamide films (e.g., nylon), ceramic materials; glass fibers; films of polyvinyl chloride; and combinations of polyvinyl chloride-silica. An especially preferred membrane material is glass fiber or nylon.

Although the thickness of the membrane may vary depending upon type of test device and the size of the sample, the typical thickness is within the range from 0.1–1.0 mm. The pores of the membrane should be of sufficient size to allow a liquid phase to freely pass through them such as by capillary action. The typical mean pore size of the membranes is between 0.1 $\mu$m and 20 $\mu$m.

By the phrase "membrane-based test device" as used herein is meant a test device that employs a membrane and one or more reagents to detect the presence and/or concentration of an analyte of interest in a test solution, preferably an aqueous test solution. At least one of the reagents associated with the membrane-based test device is a binding partner of the analyte of interest By the phrase "test solution, " as used herein, is meant a solution of which a component is a biological fluid, such as extracted, diluted, or concentrated from a plant or animal, preferably a mammal, more preferably a human. Especially preferred biological fluids are serum, plasma, urine, ascites fluid, peritoneal fluid, amniotic fluid, synovial fluid, cerebrospinal fluid and the like, or a concentrate or dilution thereof.

By the phrase, "aqueous test solution, " as used herein is meant a solution wherein more than 50% of the solvent is water, preferably more than 75%, and more preferably greater than 90% and most preferably, greater than 95%. The balance of solvent in the aqueous based solution is a non-interfering water miscible organic solvent. Typical water miscible organic solvents include alcohols having from 1 to 3 carbon atoms, polyols, such as ethylene or propylene glycol, or glycerine, polyethylene glycols having a molecular weight ("MW") from 200–600, acetone, tetrahydrofuran (THF), dimethylsulfoxide (DMSO) and the like. Other water miscible organic solvents are well known to those of ordinary skill in the art.

Typically, membrane-based test devices are of the dipstick type, the immunochromatography type, or the ICON ® or immunosorbent type. Each of these types of membrane-based devices is well known to the art. For example, U.S. Pat. No. 4,059,407 (Hochstrasser), which is incorporated herein by reference, teaches a dipstick type device. U.S. Pat. Nos. 4,632,901, 4,727,019 and U.S. Ser. No. 378,477, which are incorporated herein by reference and commonly assigned with the present invention, teach a variety of ICON ® type devices.

More specifically, the '901 and '019 patents describe an apparatus for the detection of a target antigen in a liquid sample, comprising: (a) a first member which is a porous membrane or filter and to which is bound an antibody against the target antigen, which member has upper and lower surfaces, the sample being applied to the upper surface, and wherein the antibody is bound within an area smaller than the area of the member to which the sample is applied; and (b) a second member, which is a body of absorbent material having a surface over which the first member is placed and having capillaries therethrough in a direction generally transverse to the surface over which the first member is laced, which capillaries are in communication with the pores on the lower surface of the first member so as to draw liquid added to the upper surface which has permeated the first member into the capillaries of the member, the capillary communicating between said first and second members having been established prior to, and maintained during, the addition of liquids to the apparatus in the immunoassay process.

Another such device is the TestPack ® device of Abbott Laboratories (North Chicago, Ill.) described in European Patent Application No. 217,403, published Apr. 8, 1987. Still other membrane-based devices include the devices of Bauer, et al., U.S. Pat. No. 3,811,840, issued May 21, 1974; Brown, III, et al., U.S. Pat. No. 4,916,056, issued Apr. 10, 1990; Cole, et al., U.S. Pat. No. 4,407,943, issued Oct. 4, 1983; Cole, et al., U.S. Pat. No. 4,246,339, issued Jan. 20, 1981; Intengan, U.S. Pat. No. 4,440,301, issued Apr. 3, 1984; Jolley, U.S. Pat. No. 4,704,255, issued Nov. 3, 1987; Katz, et al., U.S. Pat. No. 4,496,654, issued Jan. 29, 1985; and Tom, et al., U.S. Pat. No. 4,366,241, issued Dec. 28, 1982, all of which are incorporated herein by reference.

Membrane-based devices of the immunochromatography type are taught in Weng, et al., U.S. Pat. No. 4,740,468, issued Apr. 26, 1988, which is incorporated herein by reference, and published European Application No. 186,100 to Yue, et al., published Jul. 2, 1986. Yet other membrane-based devices of the immunochromatography type are described in U.S. Pat. No. 4,861,711, issued Aug. 29, 1989 to Friesen, et al.; U.S. Pat. No. 4,855,453, issued Aug. 8, 1989 to Rosenstein, et al.; U.S. Pat. No. 4,857,453, issued Aug. 15, 1989 to Ullman, et al., all of which are incorporated herein by reference, and May, et al., EPO Publication No. 291,194, published Nov. 17, 1988; Ching, et al., EPO Publication No. 299,428, published Jan. 18, 1989, and Devereaux, et al., EPO publication No. 323,605, published Jul. 12, 1989.

The stabilized internal calibrator of the present invention is useful with any of these membrane-based devices. A particularly preferred use for the stabilized internal calibrator of the present invention is as an internal calibrator on a membrane-based device that has an application in diagnostic and/or veterinary medicine.

The choice and size of a microparticle for the stabilized internal calibrator of a membrane-based device is influenced by the choice of material for the membrane and whether the calibrator is to be immobilized on the membrane by entrapment within its pores or by affixation to its matrix.

The stabilized internal calibrator of the present invention may be affixed to the membrane by covalent or non-covalent bonding. One technique for covalently bonding the internal calibrator of the present invention to a membrane is membrane activation. In membrane activation, the functional groups on the membrane or on a portion thereof are chemically activated to covalently bind to the binding pair (e.g., a protein) that has been immobilized on the microparticle. For example, the hydroxyl groups on a membrane, such as a cellulosic membrane, may be activated with a cyanogen halide such as cyanogen bromide. The activated hydroxyl groups are then capable of covalently coupling to an amino group, such as an $\epsilon$-amino group, on the calibrator of the present invention to produce one or more isourea linkages (i.e., covalent bonds) that are capable of affixing the calibrator to the membrane. The membrane activation technique offers the greatest versatility in calibrator size because it is capable of binding calibrators of the present invention ranging in size from those small enough to pass through the membrane, to those that are too large to become entrapped in the membrane's pores.

It is also within the scope of the present invention that the stabilized internal calibrator be affixed to the membrane by non-covalent means. For example, it is known that latex particles passively affix themselves to the fibers of a glass fiber membrane by an unknown mechanism. Because of this passive fixation, one may use calibrators of the present invention that are substantially smaller in diameter than the mean pore size of the glass fiber membrane.

Preferably, the stabilized internal calibrator of the present invention is trapped in the pores of the membrane component of a membrane-based test device. To entrap a stabilized internal calibrator of the present invention in the pores of a membrane, the pore sizes of the membrane must span a range that includes openings large enough to allow a substantial number of calibrator particles of a predetermined size to enter the membrane and restrictions within the pores of a size that are small enough to entrap the calibrator particles that have migrated therein. The pore sizes of membranes are reported by membrane manufacturers as a mean pore size having an upper and a lower limit.

The portion of the membrane where the stabilized internal calibrator of this invention is entrapped or affixed is known as a calibrator zone. Preferably, the calibration zone, which contains the stabilized internal calibrator of the present invention, is located on a discrete portion of the membrane of a membrane-based test device. When the membrane-based test device is of the ICON ® type, the membrane is preferably nylon and the microparticle component is preferably polystyrene. When the membrane-based test device is of the immunochromatography type, the membrane is preferably nitrocellulose and the microparticle component is preferably polystyrene.

To produce a calibration zone on the membrane of a membrane-based test device, a precisely measured and predetermined volume (i.e., "aliquot") of a well-mixed suspension containing the stabilized internal calibrator is deposited on a predetermined portion ("zone") of the membrane of a membrane-based test device. Techniques for precisely depositing (or "spotting") a predetermined volume of liquid on a discrete area of a membrane are well known in the art. Such precision techniques include micropipetting and jet-spraying. The latter is also known as jet-printing.

The micropipetting technique is well suited for depositing a precise amount of the calibrator of the present invention in the form of a spot or a circle to produce a circular calibration zone on the membrane of a membrane-based device. The circular calibration zone is well suited for use with the membrane-based device of the ICON® or the immunosorbent type. One method of spotting employs a mechanical means, such as the Sandy Springs Spotting Machine (Germantown, Md.), for applying a suspension (e.g., latex) to a membrane. Another method of spotting employs a hand held micropipettor that is capable of depositing a fixed volume, typically 2–10 $\mu$l, of a suspension containing the stabilized internal calibrator of the present invention. A description of the hand spotting technique is provided in Example 4.

For the precise printing of a calibration zone having a particular geometric or non-geometric shape or for uniformly covering an area, the jet spraying technique is preferred. Use of the jet spraying technique for depositing microparticles is taught in U.S. Pat. No. 4,877,745, which issued on Oct. 31, 1989 and is incorporated herein by reference.

In its second aspect, the present invention is directed to a method for making a stabilized internal calibrator for a membrane-based test device. The method of the present invention comprises the steps of:

a. allowing a first binding partner of the analyte of interest and the analyte of interest to form a binding pair;

b. either before or after Step (a), bonding the first binding partner to a microparticle, whereupon after the combination of Steps (a) and (b), an immobilized binding pair is formed; and c. reacting the immobilized binding pair with an effective amount of a cross-linking agent for covalently cross-linking the analyte of interest and the binding partner of the immobilized binding pair to one another such that an effective amount of the analyte of interest immobilized thereon becomes substantially fixed thereon, the effective amount of the analyte of interest also having an area on its surface or a cavity sufficiently exposed to be capable of participating in the formation of an immobilized second binding pair with a second binding partner.

Preferably, the second binding partner is a labeled binding partner, more preferably, a labeled monoclonal antibody. When the first binding partner is a monoclonal antibody, the second binding partner is preferably also a monoclonal antibody; more preferably a monoclonal antibody that has specificity for a second binding site (i.e., epitope) on the analyte of interest, the second binding site being positioned substantially opposite to the binding site for the first binding partner. In the latter embodiment, the first monoclonal antibody (i.e., the first binding partner) binds to the analyte of interest and uniformly positions the analyte relative to itself such that the binding site on the analyte for the second monoclonal antibody is substantially unhindered by the first monoclonal antibody.

The label on the second binding partner may be any chemical substance or particle that is capable of being detected either visually, or instrumentally. When the label is a chemical substance, the chemical substance may be a dye, a dye precursor, a chemiluminescent, a phosphorescent or a fluorescent agent, an enzyme, an enzyme substrate or a radioisotope. A variety of these chemical labels are known to those of ordinary skill in the art. For example, see U.S. Pat. No. 4,366,241 (Tom) which teaches a variety of dyes, fluorescent agents, enzymes, chemiluminescers, and radioisotopes, all of which is incorporated herein by reference.

The use of enzymes as labels has long been known to the art. Typical enzyme labels include: alkaline phosphatase, horseradish peroxidase, luciferase, $\beta$-galactosidase, glucose oxidase, lysozyme, malate dehydrogenase, glucose-6-phosphate dehydrogenase, and the like. The enzyme label may be used alone or in combination with a second enzyme that is in solution. One dual enzyme system includes the enzymes alkaline phosphatase and glucose oxidase wherein glucose-6-phosphate is used as the initial substrate. A dual catalyst system that uses a single enzyme is illustrated by the oxidation of glucose to hydrogen peroxide by glucose oxidase, which hydrogen peroxide would react with a leuco dye to produce a signal generator. A more detailed discussion of enzyme labels can be found, for example, in U.S. Pat. No. 4,366,241 to Tom, et al., particularly columns 27–40; U.S. Pat. No. 4,843,000, issued Jun. 27, 1989 to Litman, et al.; and U.S. Pat. No. 4,849,338, issued Jul. 18, 1989 to Litman, et al., all of which are incorporated herein by reference. Also, see Weng, et al., U.S. Pat. No. 4,740,468, which is also incorporated herein by reference, especially at columns 2 and 6–8.

The procedure for coupling an enzyme label to a binding partner are well known in the art and are described, for example, in Kennedy, et al., *Clin. Chim. Acta* 70:1 (1976). Reagents that may be used for this procedure include, for example, glutaraldehyde, p-toluene diisocyanate, various carbodiimide reagents, p-benzoquinone m-periodate, N,N'-o-phenylenedimaleimide and the like.

When the label is a particle, it may be a colored colloid, a liposome sac with a hydrophobic dye therein, or a colored latex particle. The use of a colored colloidal label, such as colloidal gold or selenium, is taught for example in U.S. Pat. No. 4,313,734, which issued Feb. 2, 1982 to Leuvering; and U.S. Pat. No. 4,775,636, which issued Oct. 4, 1988 to Moermans, et al.; both of which are incorporated herein by reference, and Yost, et al., EPO Pub. No. 298,368, published Jan. 11, 1989.

The use of a label comprising liposomal sacs containing aqueous dispersions of a hydrophobic dye or pigment is taught in U.S. Pat. No. 4,703,017 (Campbell) which is incorporated herein by reference.

Colored latex particles are commercially available in a variety of colors from red to violet, including black, white, gray and fluorescent, and in sizes ranging from 0.038 $\mu$m to 15.3 $\mu$m, such as from Bangs Laboratories, Carmel, Ind. The use of colored particles as a marker is described in U.S. Pat. No. 4,373,932 (Gribnau et al.) which is incorporated herein by reference. The binding of a latex particle to a binding partner is already taught herein. When a colored latex particle is used as the label, it must be small enough to pass through the pores of the membrane in the membrane-based device. Colored latex particles that are too large would become trapped in the membrane and give rise to a background color. By selecting colored latex particles that are small enough to pass through the membrane, the retention of colored latex particles on the membrane reflects formation of a second binding pair.

A preferred labeling system uses the enzyme alkaline phosphatase and 5-bromo-4-chloro-3-indoxyl phosphate as its substrate to produce an indigo blue color. See for example, Horowitz, et al., *J. Med. Chem.*, 9, 447 (1966) which is incorporated herein by reference. For greater color intensity, the substrate solution may optionally contain a tetrazolium salt which is reduced to a formazan dye during the oxidation of the cleaved indoxyl substrate. The indoxyl-tetrazolium method is taught by Moe et al., "Evaluation of The Indoxyl-Tetrazolium Method for Measurement of Alkaline Phosphatase Activity, " *Cell and Mol. Biol.*, 28 555–558 (1982) which is incorporated herein by reference. A preferred alkaline phosphatase enzyme is (EC 3.1.3.1) which is derived from calf intestine. When the above enzyme system is used, the color is capable of being determined visually as well as instrumentally.

To obtain a qualitative result on a membrane-based test device that employs a stabilized internal calibrator of the present invention, one compares the signals produced at the test zone and the calibration zone of the membrane. In some assays, any detectable signal in the test zone is interpreted as a positive result indicating the presence of the analyte of interest. In other assays, the signal in the test zone must be equal to or greater than the signal in calibration zone. This latter assay is known as a semi-quantitative assay because the result is obtained by comparing the signal level at the test zone versus a known concentration of analyte that is associated with the signal at the calibration zone. Any signal in the test zone that is above the calibration signal indicates a concentration of analyte in the test zone that is greater than the concentration of analyte in the calibration zone. A preferred signal is a colored signal, more preferably, a colored signal that is capable of visual assessment.

To obtain a quantitative result on a membrane-based device that employs a stabilized internal calibrator of the present invention, one utilizes an appropriate instrument to measure the signal intensity produced at the calibration zone by a predetermined concentration of analyte and compares that to the signal intensity measured at the test zone to obtain the unknown concentration of analyte in the test zone. Measurement of the signal may be made by any instrument that is capable of converting the signal into a digital expression that is proportional to the signal produced. Depending on the nature of the label and catalytic signal producing system, a signal can be instrumentally detected by irradiating a fluorescent label with light and measuring the level of fluorescence in a fluorometer, by providing for an enzyme system to produce a dye, fluorescence, or chemiluminescence, where the dye can be measured in a spectrophotometer or reflectometer, the fluorescence could be measured in a fluorometer, or in the case of chemiluminescence or a radioactive label, by employing a radiation counter.

A preferred signal for quantitation is a colored signal and a preferred method of measurement is reflectance such as taught in Anderson et al. "Internally Referenced ImmunoConcentration Assays," Clin. Chem., 32 (1692–1695 (1986) which is incorporated herein by reference. Reflectance relies upon the Kubelka-Munk relationship:

$$\frac{K}{S} = \frac{(1 - R\infty)^2}{2 R\infty} = \frac{\epsilon C}{S}$$

where K=the absorption coefficient, S=the scattering coefficient, $R\infty$ =the diffuse reflectance, $\epsilon$=the absorptivity coefficient and C=the concentration of the absorbing species. After measuring the diffuse reflectance of the calibration zone, the K/S ratio is calculated and plotted against the concentration of analyte in the calibration zone to generate a number that can be used to calculate the concentration of analyte in the test zone based upon the measured diffuse reflectance and calculated K/S for the test zone. For a quantitative assay the concentration of calibrator in the calibration zone is preferably selected to have a value of about 1.0.

EXPERIMENTAL SECTION

1. Preparation of a Stabilized Internal Calibrator for a Membrane-Based Test Device for the Analyte CK-MB A. Passive Adsorption (Bonding) Of Anti CK-B Onto Latex Microspheres To 0.093 ml of monoclonal anti CK-B (0.500 mg/ml), which was prepared according to Example 5, was added 0.788 ml of 0.025M MES (2-(N-morpholino)-ethane sulfonic acid, sodium salt buffer), pH 5.0. To this solution was added 0.119 ml of an 8.4% latex suspension (polystyrene microspheres) having a 1 $\mu$m mean diameter. The reaction mixture was incubated for two hours with gentle stirring at 45° C. Historically, a 50% uptake of antibody by the latex was obtained.

B. Formation Of An Immobilized Binding Pair Comprising Latex: Anti CK-B: CKMB

A 1 ml aliquot of the 1% latex (antibody coated) suspension from Example (1)(A) was calculated to contain $1.67 \times 10^{-9}$ moles of immobilized antibody. This suspension was centrifuged for 15 minutes and the supernatant removed. A 1 ml solution containing 5 $\mu$g of CK-MB that had been diluted from stock (Hybritech P/N 220432 "CKMBII stock standard") with 20 mM PBS was used to resuspend the antibody coated latex. The resulting suspension was incubated for thirty minutes at 37° C. Thereafter, the mixture was centrifuged for 15 minutes and the supernatant removed. The pellet was resuspended in 1 ml of 20 mM PBS and centrifuged for 15 minutes. The supernatant was again discarded and the pellet was resuspended in 20 mM PBS. The resulting suspension contained the immobilized binding pair, latex:anti CK-B:CK-MB.

C. Cross-Linking The Immobilized Binding Pair With Disuccinimidyl Suberate

To test for a possible gain in the stability of an immobilized binding pair as prepared in Example (1)(B) above, two additional preparations of the immobilized binding pair were subjected to a 10:1 and a 100:1 ratio of cross-linking agent to protein. The cross-linking agent was disuccinimidyl suberate ("DSS"), Pierce Chemical Co., Rockford, Ill.

a. Preparation Of Control A

A suspension of the immobilized binding pair as prepared in Example (1)(B) was centrifuged for 15 minutes and the supernatant discarded. The pellet was washed by resuspension in 20 mM PBS and thereafter centrifuged for 15 minutes. The supernatant was again discarded and the washed pellet was resuspended in 3 mls of 20 mM PBS sucrose.

b. Preparation B: Cross-Linking The Product Of Example (1)(A) Using 10x DSS

A suspension of the immobilized binding pair as prepared in Example (1)(B) was centrifuged for 15 minutes and the supernatant decanted. The pellet was resuspended in 20 mM PBS. The suspension was estimated to contain $5.0 \times 10^{-9}$ moles of protein. To 5 mg of DSS in a serum vial was added 900 μl of acetonitrile, not sooner than 5 minutes before use. To the resuspended pellet was added 3.33 μl of the freshly prepared DSS (i.e., $5.0 \times 10^{-8}$ moles DSS). The mixture was vortexed and incubated at room temperature, preferably 25° C., for 30 minutes. Thereafter, the mixture was centrifuged for 15 minutes and the supernatant discarded. The remaining pellet was washed by resuspension in 20 mM PBS, centrifuged, and the supernatant discarded. The remaining pellet, which was composed of the immobilized and now cross-linked binding pair, was resuspended in 20 mM PBS with sucrose.

c. Preparation C: Cross-Linking The Product Of Example (1)(A) Using 100 X DSS

Preparation C was prepared as for Preparation B above, with the exception that a suspension of the immobilized binding pair of Example (1)(B) was reacted with 33.3 μl of the freshly prepared solution of DSS (i.e., 5 mg DSS in 900 μl acetonitrile) which provided $5.0 \times 10^{-7}$ moles of DSS as a cross-linking agent.

Results

Preparations A and B were resuspended in 20 mM PBS, or PBS containing 10% Sucrose (hereinafter "PBS sucrose"). However, Preparation C, which used 100x DSS, would not resuspend in PBS sucrose. This resuspension issue was later resolved via quenching or "capping" of the cross-linking reaction through the addition of Ethanolamine to 20 mM final concentration followed by incubation at room temperature for 15 minutes followed by washing and resuspension in PBS sucrose.

The preferred parameters for preparation of the DSS cross-linked latex:anti CK-B:CK-MB are as follows:

| | |
|---|---|
| Processing Vessel: | Centrifuge Tube |
| Antibody Incubation Time: | 27–33 minutes |
| Antibody Concentration: | 500 μg/ml |
| Antigen Concentration: | 57 μg/ml |
| DSS Concentration: | 0.8 mM |
| Suspension Buffer: | 20 mM PBS/10% Sucrose with 0.5% BSA |

2. Cross-Linking the Immobilized Binding Pair of Example (1)(B) with DFDNB, DMA and DMP The immobilized binding pair of Example (1)(B) was separately cross-linked with a 10:1 and a 100:1 molar ratio of cross-linking agent to protein for each of the above identified agents. In the reactions that follow, the amount of protein on the microparticles in the volume of suspension was estimated at $5.0 \times 10^{-9}$ moles. Accordingly, $5.0 \times 10^{-8}$ moles of cross-linker was employed in the 10:1 ratio and $5.0 \times 10^{-7}$ moles was employed in the 100:1 ratio.

A. Cross-Linking with DMA and DMP

Four preparations of the product of Example (1)(B), which are designated as V, VI, VII and VIII, were centrifuged for 15 minutes and the supernatant discarded. The pellets were resuspended in triethanolamine. Stock solutions of dimethyl adipimidate ("DMA") and dimethyl pimelimidate ("DMP") were prepared within 5 minutes of use by respectively diluting 0.005 g of DMA and DMP in 1.4 ml and 1.3 ml of triethanolamine respectively. To preparations, V, VI, were added 3.33 ml and 33.3 ml respectively of the freshly prepared DMA solution. To preparations VII and VIII were added 3.33 and 33.3 μl respectively of the freshly prepared DMP solution. Each of the preparations was incubated for 30 minutes and then quenched with a 40x excess of ethanolamine to cross-linker. The preparations were centrifuged for 15 minutes and the supernatant discarded. The pellets were resuspended in 20 mM PBS respectively, recentrifuged for 15 minutes, and their supernatants removed respectively. To the remaining pellets were added 3 ml of PBS sucrose and the pellets were resuspended.

B. Cross-Linking With DFDNB

Two preparations of the product of Example (1)(B), which are designated as III and IV. respectively, were centrifuged for 15 minutes and the supernatant discarded. The pellets were each resuspended in 1.0 ml of 20 mM PBS. Five minutes prior to use, a stock solution of DFDNB was prepared by diluting 0.005 g of difluorodinitrobenzene ("DFDNB"), such as available from Sigma Chemical Co., St. Louis, Mo., to 1.6 ml of acetonitrile. To resuspended preparations III and IV was added 3.33 μl (i.e., 10x) and 33.3 μl (i.e., 100x) of the freshly prepared DFDNB solution. The reaction mixtures were mixed and then incubated for thirty minutes at 25° C. Thereafter, Preparations III and IV were quenched by adding 40 μl and 400 μl respectively of ethanolamine and mixing for 15 minutes. The reaction mixture was centrifuged and the supernatant decanted. The pellet was resuspended in 20 mM PBS. The suspension was again centrifuged for 15 minutes and the supernatant decanted. The pellet containing the cross-linked and immobilized binding pair was finally resuspended in 20 mM PBS sucrose.

Results

The cross-linked and immobilized binding pairs of this example were compared for stability over a five day period at 4° C., 25° C., and 35° C. relative to uncrosslinked immobilized binding pairs as controls. Over a five day period, none of the cross-linked calibrators out performed the control when stored at 4° C. or at 25° C. However, at 35° C., the calibrators that were cross-linked with DMA and DMP showed a slight increase in stability. The calibrator that was cross-linked with DFDNB was less stable than the control at 0° C., 25° C. and at 35° C.

3. Preparation of Cross-Linked Calibrators for CK-MB using 100:1, 300:1 and 900:1 Ratios of Cross-Linker to Immobilized Protein Using DMA, DMP and DMS (dimethylsuberimidate) as the cross-linking agents, nine preparations of the immobilized binding pair of Example (1)(A), (i.e., latex: anti CK-B:CK-MB) were cross-linked according to the procedure of Example (2)(A) using 100:1, 300:1 and 900:1 ratios of cross-linker to immobilized protein for each of the three cross-linkers. During the post quench wash, the preparation with the 300:1 and 900:1 ratios of DMP and DMS showed signs of clumping.

Results

The immobilized binding pairs of Example (1)(B) that were cross-linked with 900:1 ratios of DMP and DMS respectively showed an increase in liquid latex stability over a 5 day period relative to the immobilized pair of Example (1)(B) as a first control and an immobilized pair of Example (1)(B) that was subject to the reaction conditions and solvents but not the cross-linking agent as a second control. The increase in stability for DMP and DMS at 900:1 appeared less than that obtained with DSS at 100:1.

4. Handspotting of the Stabilized Internal Calibrator

A stabilized internal calibrator, such as described in Example 1, is suspended in 20 mM PBS 10% sucrose with 0.5% bovine serum albumin (BSA) at a concentration of 0.333% W/W. A digital precision pipet such as a Pipetman P-20 (a product of Rainin Instrument Co., Woburn, Mass.) or Eppendorf Ultra Micro Pipet (a product of Brinkmann Instruments, Inc. Westbury, N.Y.) is then adjusted to a volume of 4 $\mu$l and a disposable tip attached. The suspension of microparticles is vortexed once for 5–10 seconds and the pipet is immediately used to draw in 4 $\mu$l of the suspension. Holding the pipet steadily with both hands, the suspension of microparticles is then deposited on the membrane-based test device from a height of approximately 2–3 cm. It is allowable to "touch off" the drop of fluid on the membrane to coat it evenly. The membrane-based test device should then be allowed to dry for 1–2 hours before use. Store the spotted membrane-based test device in a sealed container with a small amount of dessicant.

5. Propatation and Isolation of a Monoclonal Antibody for the B Subunit Kinase

BALB/c mice were immunized with a purified preparation of human creatine kinase BB antigen (hereinafter CKBB) which is commercially available from Scripps Laboratories, Inc., San Diego, Calif., Cat. No. C1124. Spleen cells from the immunized mice were fused with the mycloma cell line P3,653 by the polyethylene glycol procedure of Gerhard as disclosed in "Monoclonal Antibodies And Hybridomas: A New Dimension in Biological Analyses," Ed. R. H. Kennett et al., Plenum Press, N.Y. 1980, pp. 370–371 which is incorporated herein by reference. After fusion, the resultant hybridoma cells were plated into 96 well microtiter plates in HAT (hypoxanthine/aminopterin/thymidine) media. The culture supernatants were preliminarily screened for antibody production via the microtiter ELISA technique using immobilized CKBB antigen.

The antibody cell lines were subcloned by limiting dilution, i.e., a concentration of cells of less than 1 cell/well, to ensure monoclonality. In order to select the specific antibody to be used in the present invention, antibodies were screened by a microtiter plate ELISA procedure for their ability to preferentially bind purified CKBB (which was immobilized on the microtiter plates as noted above) compared to control wells wherein creatine phosphokinase MM antigen (hereinafter CKMM) was immobilized. Hybridoma culture supernatants of antibodies found to be highly reactive and specific for CKBB were further characterized for affinity, genetic stability, and performance in a two-site immunometric assay. The hybridoma cell line producing the monoclonal antibody for the present invention was designated CK4F253.4.

The monoclonal antibody from cell line CK4F253.4 was purified by an ion exchange chromatography on Q-SEPHAROSE ® Fast Flow brand ion exchange resin (Pharmacia, Piscataway, N.J.) using a linear salt gradient (from 0.01M to 0.50M NaCl) in 0.02M Tris buffer pH 8.2. See "FPLC: Ion Exchange and Chromatofocusing, Principles and Methods," (i.e., The Pharmacia Handbook) Pharmacia, 1985, which is available from Pharmacia, Piscataway, N.J. The resulting purified monoclonal antibody was designated as anti CK-B monoclonal antibody.

What is claimed is:

1. A method for determining the presence or amount of an analyte of interest that has at least a first and a second sterically separate antigenic sites, said method comprising:
    (a) providing a reactive membrane comprising a calibration zone and a test zone, wherein said calibration zone is provided by
        (i) immobilizing a predetermined amount of a first antibody on a plurality of microparticles, wherein said first antibody is an antibody or immunoreactive fragment thereof capable of specifically binding to said first antigenic site on said analyte, in order to form a first immobilized antibody;
        (ii) contacting a first portion of said first immobilized antibody with a predetermined amount of said analyte to form a plurality of first immobilized specific binding pairs;
        (iii) reacting said first immobilized specific binding pairs with an amount of a covalent cross-linking agent effective to cross-kink said first immobilized antibody such that any remaining specific binding sites on said first immobilized antibody are substantially incapable of further specifically binding to any additional analyte, but at least some of said analyte is capable of specifically binding to a preselected amount of a labelled second antibody, wherein said labelled second antibody is a directly or indirectly labelled antibody or immunoreactive fragment thereof capable of specifically binding to said second antigenic site; and,
        (iv) immobilizing said cross-linked immobilized specific binding pairs of step (a) (iii) in said calibration zone;
    and wherein said test zone is provided by immobilizing a second portion of said first immobilized antibody in said test zone;
    (b) contacting said reactive membrane with a test sample in order to specifically bind any said analyte of interest in said test sample to said immobilized first antibody in said test zone;
    (c) contacting said reactive membrane of step (b) with said labelled second antibody; and
    (d) determining the presence or amount of said analyte in said test sample by comparing the amount of labelled second antibody specifically bound in said test zone with the amount of labelled second antibody specifically bound in said calibration zone.

2. The method of claim 1 wherein said first antibody is a monoclonal antibody.

3. The method of claim 2 wherein said microparticles are either glass or polymeric microspheres.

4. The method of claim 3 wherein said microparticles have a mean diameter within the range of 0.01 μm to 100 μm.

5. The method of claim 2 wherein said microparticles are microspheres that are members of the group consisting of polystyrene, butadiene styrene, styrene-acrylic-vinyl carboxylate terpolymer, polymethylmethacrylate, polyethylmethacrylate, styrene-maleic anhydride copolymer, polyvinylacetate, polyvinylpyridine, polydivinyl benzene, acrylonitrile, vinyl chloride acrylates, and a carboxylate or an amino derivative thereof.

6. The method of claim 5 wherein said polymeric microspheres have a mean diameter of about 0.1 μm to about 75 μm.

7. The method of claim 6 wherein the polymeric microspheres are polystyrene or a carboxylate or an amino derivative thereof.

8. The method of claim 7 wherein the cross-linking agent is either a homobifunctional cross-linking agent or a heterobifunctional cross-linking agent.

9. The method of claim 8 wherein the cross-linking agent is a member of the group consisting of disuccinimidyl suberate, dimethyl adipimidate, dimethyl pimelimidate, and dimethyl suberimidate.

10. The method of claim 9 wherein the analyte of interest is CK-MB.

11. The method of claim 10 wherein the first antibody is a monoclonal antibody that has specificity for the B subunit of creatine kinase.

12. The method of claim 11 wherein the labelled second antibody is a directly labelled second antibody.

13. The method of claim 12 wherein the directly labelled second antibody is a directly labelled monoclonal antibody.

14. The method of claim 2 wherein said labelled second antibody comprises a monoclonal antibody or an immunoreactive fragment thereof.

15. The method of claim 14 wherein said labelled second antibody is a directly labelled second antibody.

16. The method of claim 15 wherein said label is a member of the group consisting of a dye, a dye precursor, a chemiluminescent agent, a phosphorescent agent, a fluorescent agent and an enzyme.

17. The method of claim 16 wherein said label is an enzyme that is a member of the group consisting of alkaline phosphatase, horseradish peroxidase, luciferase, β-galactosidase, glucose oxide, lysozyme, malate dehydrogenase, and glucose-6-phosphate dehydrogenase.

18. The method of claim 17 wherein the enzyme is alkaline phosphatase.

19. The method of claim 18 wherein a substrate for the enzyme is 5-bromo-4-chloro-3-indoxyl phosphate.

20. The method of claim 14 wherein said label is a particle that is a member of the group consisting of colloidal gold, colloidal selenium, a liposomal sac and a colored latex particle.

* * * * *